(12) United States Patent
Swoyer et al.

(10) Patent No.: US 7,729,781 B2
(45) Date of Patent: Jun. 1, 2010

(54) HIGH EFFICIENCY NEUROSTIMULATION LEAD

(75) Inventors: John M. Swoyer, Andover, MN (US); Jeffrey S. Gagnon, Champlin, MN (US)

(73) Assignee: Greatbatch Ltd., Clarence, NY (US)

( * ) Notice: Subject to any disclaimer, the term of this patent is extended or adjusted under 35 U.S.C. 154(b) by 283 days.

(21) Appl. No.: 11/686,322

(22) Filed: Mar. 14, 2007

(65) Prior Publication Data

US 2007/0219608 A1      Sep. 20, 2007

Related U.S. Application Data

(60) Provisional application No. 60/782,819, filed on Mar. 16, 2006.

(51) Int. Cl.
*A61N 1/05* (2006.01)
(52) U.S. Cl. ........................................ 607/116; 607/118
(58) Field of Classification Search ................... 607/96, 607/101–102, 115–122, 1–45, 129, 137; 600/373, 377, 381, 12; 514/27, 283, 34, 514/449, 575; 128/639–642; 606/117; 424/423
See application file for complete search history.

(56) References Cited

U.S. PATENT DOCUMENTS

| | | | | |
|---|---|---|---|---|
| 4,044,774 A | | 8/1977 | Corbin et al. | |
| 4,515,162 A | * | 5/1985 | Yamamoto et al. | 600/391 |
| 4,538,624 A | * | 9/1985 | Tarjan | 600/517 |
| 5,002,067 A | * | 3/1991 | Berthelsen et al. | 607/120 |
| 5,103,837 A | | 4/1992 | Weidlich et al. | |
| 5,257,634 A | * | 11/1993 | Kroll | 607/122 |
| 5,265,608 A | * | 11/1993 | Lee et al. | 600/377 |
| 5,324,324 A | | 6/1994 | Vachon et al. | |
| 5,345,933 A | | 9/1994 | Peterson et al. | |
| 5,554,179 A | * | 9/1996 | Stroetmann et al. | 607/129 |
| 5,713,847 A | * | 2/1998 | Howard et al. | 604/21 |
| 6,078,841 A | * | 6/2000 | Kuzma | 607/137 |
| 6,292,702 B1 | * | 9/2001 | King et al. | 607/116 |
| 6,304,787 B1 | * | 10/2001 | Kuzma et al. | 607/137 |
| 6,487,453 B1 | * | 11/2002 | Kuzma et al. | 607/137 |
| 6,529,774 B1 | * | 3/2003 | Greene | 600/545 |
| 6,856,840 B2 | * | 2/2005 | Munshi | 607/121 |
| 6,981,314 B2 | * | 1/2006 | Black et al. | 29/825 |
| 7,152,131 B2 | * | 12/2006 | Saen et al. | 710/307 |

(Continued)

OTHER PUBLICATIONS

Kim et al. (2006): "Sustained release of dexamethasone from hydrophilic matrices using PLGA nanoparticles for neural drug delivery." Biomaterials 27 (2006) 3031-3037. (Available online Jan. 2006).*

(Continued)

*Primary Examiner*—Carl H Layno
*Assistant Examiner*—Paula J Stice
(74) *Attorney, Agent, or Firm*—Michael F. Scalise

(57) ABSTRACT

Devices and methods for stimulating nerves, such as peripheral nerves are described. Some devices can include small cross-section lead bodies having one or more electrodes in the round distal portion, the electrodes having a substantially planar surface within the distal portion of the lead which is suitable for placement through a cylindrical needle intended to access a spinal region of a patient. Some lead electrodes are covered with a hydrophilic coating at least about 0.001 inches thick. The hydrophilic coating may include a steroid and/or a GABA (gamma-aminobutyric acid) agonist which can elute or diffuse over time, away from the electrode.

34 Claims, 4 Drawing Sheets

U.S. PATENT DOCUMENTS

| | | | | |
|---|---|---|---|---|
| 7,282,213 | B2* | 10/2007 | Schroeder et al. | 424/422 |
| 2001/0025192 | A1* | 9/2001 | Gerber et al. | 607/117 |
| 2002/0045926 | A1* | 4/2002 | Heil et al. | 607/116 |
| 2002/0077684 | A1* | 6/2002 | Clemens et al. | 607/116 |
| 2002/0077685 | A1* | 6/2002 | Sundquist et al. | 607/116 |
| 2002/0138123 | A1* | 9/2002 | Casas-Bejar et al. | 607/120 |
| 2003/0045919 | A1* | 3/2003 | Swoyer et al. | 607/122 |
| 2004/0260310 | A1* | 12/2004 | Harris | 606/117 |
| 2005/0049663 | A1 | 3/2005 | Harris et al. | |
| 2005/0096718 | A1* | 5/2005 | Gerber et al. | 607/117 |
| 2005/0096751 | A1* | 5/2005 | Gerber et al. | 623/23.66 |
| 2005/0113899 | A1* | 5/2005 | Cross, Jr. | 607/122 |
| 2005/0175665 | A1* | 8/2005 | Hunter et al. | 424/423 |
| 2005/0192644 | A1* | 9/2005 | Boveja et al. | 607/45 |
| 2005/0240238 | A1* | 10/2005 | Mamo et al. | 607/39 |
| 2006/0052656 | A1* | 3/2006 | Maghribi et al. | 600/12 |
| 2006/0129218 | A1* | 6/2006 | Swoyer et al. | 607/117 |
| 2007/0050004 | A1* | 3/2007 | Swoyer et al. | 607/116 |
| 2007/0100408 | A1* | 5/2007 | Gerber | 607/117 |
| 2007/0112404 | A1* | 5/2007 | Mann et al. | 607/116 |
| 2007/0118198 | A1* | 5/2007 | Prager | 607/116 |
| 2007/0179579 | A1* | 8/2007 | Feler et al. | 607/117 |
| 2007/0255370 | A1* | 11/2007 | Bonde et al. | 607/117 |
| 2007/0292470 | A1* | 12/2007 | Thornton | 424/423 |

OTHER PUBLICATIONS

Kim et al. (2005): "Conducting polymers grown in hydrogel scafolds coated on neural prosthetic devices." Journal of Biomedical Materials Research 71A (2005) 577-585. (Published online Oct. 27, 2004).*

Schwartz et al. (2004): Cortical Neural Prosthetics. Annual Review of Neuroscience 27 (2004) 487-506.*

Kipke (2004): "Implantable neural probe systems for cortical neuroprostheses." Proceedings of the 26th Annual International Conference of he IEEE EMBS, San Francisco, CA, USA, Sep. 1-5, 2004.*

Lagarce et al. (2005) "Baclofen-loaded microspheres in gel suspensions for the intraecal drug delivery: In vitro and in vivo evaluation." European Journal of Pharmaceutics and Biopharmaceutics 61 (2005) 171-180.*

Drake et al. (1988) "Preformance of Planar Multisite Microprobes in Recording Extracellular Single-Unit Intracortical Activity." IEEE Transactions on Biomedical Enginering 35 #9 Sep. 1988 719-732.*

Vetter et al. (2004) "Chronic Neural Recording Using Silicon-Substrate Microelectrode Arrays Implanted in Cerebral Corex." IEEE Transactions on Biomedical engineering 51 #6 Jun. 2004.*

Szarowski et al., Brain responses to micro-machined silicon devices. Brain Research 2003; 983 (1-2): 22-35.*

Rousche et al., Felxable polyimide-based intracortical electrode arrays with bioactive capability. IEEE Tansactions on Biomedical Engineering 2001; 48(3):361-371.*

Polymer Chemistry and Hydrogel Systems; E. H. Schacht, Journal of Physics: Conference Series 3 (2004) 22-28.*

* cited by examiner

HIGH EFFICIENCY NEUROSTIMULATION LEAD

RELATED APPLICATIONS

The present application is a nonprovisional of U.S. Provisional Patent Application No. 60/782,819, filed Mar. 16, 2006, titled HIGH EFFICIENCY NEUROSTIMULATION LEAD.

TECHNICAL FIELD

The present invention is related generally to medical devices. More specifically the present invention is related to neurostimulation leads.

BACKGROUND

Implantable leads, typically having externally exposed ring or band electrodes can be used to deliver electrical stimulation to surrounding tissue and/or to sense electrical energy produced by the surrounding tissue. Such leads are often implanted, for example, within the epidural or intrathecal spaces of the spinal column, along peripheral nerves, within the brain, and about the heart. Electrical stimulation of the spinal cord has been shown to be effective in relieving intractable pain in some patients. Such electrical stimulation can reduce or eliminate the use of pain relieving drugs. Examples of some leads may be found in U.S. Pat. Nos. 6,721,604; 6,981,314; 6,216,045; and 5,483,022, herein incorporated by reference.

One such lead is formed of polymeric material, for example, polyurethane or silicone. The lead can be nominally 1 mm in outer diameter and about 20 cm in length. A typical lead may have a series of electrodes formed as bands or rings disposed in a spaced apart relationship in a lead distal region. The distal region of the lead can be introduced, for example, into the epidural region for use in stimulation of the spinal column. The lead proximal region may have a corresponding set of band or ring connectors or terminals, one for each corresponding electrode in the distal region. Each proximal region terminal can thus be connected to one distal electrode in a typical configuration.

The terminals can be used to couple the proximal end of the lead to a lead extension, which can in turn be coupled to an implantable pulse generator (IPG). The lead extension can provide added length to extend the reach of the lead to a more distantly placed IPG. In some embodiments, the lead extension is between about 20 and 50 cm in length.

The lead typically has a lumen extending from the proximal end through to the distal region, with the lumen being dimensioned to accept a stiffening member or stylet. The lead, commonly formed of a polymeric material and being very small in cross section, is typically very floppy and not pushable. With a stylet or stiffening member inserted, the lead gains the needed pushability, and can be advanced into and up the spinal column to the desired location.

Current neurostimulation leads often use polished platinum electrodes having relatively large surface areas. Leads are described in U.S. Pat. Nos. 5,103,837; 5,324,324; 5,345,933; 4,044,774; and 5,265,608, herein incorporated by reference. Typical percutaneously inserted leads can use ring electrodes that wrap around 360 degrees. This is often wasteful, as energy is delivered to tissue that is not intended to be stimulated. Such wasted energy may lead to shortened battery life. This can also lead to side effects such as pain in those tissues.

What would be desirable are leads that can be percutaneously inserted and provide directional stimulation.

SUMMARY

Some embodiments of the present invention include the use of directional electrodes that can be percutaneously delivered. In some embodiments, the lead has a flat face at the distal end that predominately or only stimulates in one direction. Optionally, the electrodes can be coated with a hydrophilic polymer film, layer, or coating. The polymer absorbs body fluid, which allows the electrical charge to pass through the polymer from the metal substrate to the stimulatable tissue. This minimizes polarization of the electrodes. It may also present a more biocompatible surface to the tissue, minimizing the foreign body response to the implanted electrode.

Minimizing the response may limit the amount of fibrosis, or scar tissue that forms at the electrode surface. This type of tissue essentially acts as an insulator and increases the energy requirements of the system. Additionally, pharmaceutical agents can be included in the polymer. These agents can elute out of the polymer matrix over time and modify the tissue response to the lead. Pharmaceuticals agents in some embodiments may include steroids, for example, beclamethasone, dexamethosone, etc and their derivatives. These agents minimize the inflammatory response to the implanted foreign body.

A different class of drug that can be included in some embodiments are GABA (gamma-aminobutyric acid) agonists, for example, baclofen. These drugs enhance the ability of the stimulation to generate action potentials in the target nerves.

The present invention provides an implantable medical electrical lead including, an elongate body having a proximal portion, a distal portion, and at least one electrical conductor extending between the proximal portion and the distal portion: and a first electrode disposed in the distal portion, the first electrode having a substantially flat, planar surface and being electrically coupled to the conductor. The lead elongate body and electrode may be sized small enough in cross-sectional profile to be insertable through a 12 gauge needle. Some leads also include a hydrophilic coating over the flat electrode surface, the coating having a thickness of at least about 0.001 inch or 0.0005 inch, or between about 0.0001 and 0.01 inch, in various embodiments. The hydrophilic coating is swellable in water, in some embodiments. Some coatings include a steroid substance disposed within the hydrophilic coating for diffusion out of the hydrophilic coating. In some embodiments, the steroid is selected from the group consisting of beclamethason, dexamethosone, and their derivatives, and combinations thereof.

Some embodiment leads include a GABA agonist substance disposed within the hydrophilic coating for diffusion out of the hydrophilic coating, for example, baclofen.

The present invention also provides a method for implanting a medical electrical lead, the method including advancing an implantable medical electrical lead through a needle smaller than about 12 gauge to a target site. The lead can include an elongate body having a proximal portion, a distal portion, and at least one electrical conductor extending between the proximal portion and the distal portion. The lead may also include a first electrode disposed in the distal portion, the first electrode having a substantially flat, planar surface and being electrically coupled to the at least one conductor, where the lead elongate body and electrode are sized small enough in cross-sectional profile to be insertable through a 12 gauge needle.

DETAILED DESCRIPTION

The present invention provides leads, sized in some embodiments such that it can be delivered via a percutaneously placed needle, for example, smaller than 12 gauge, typically between 13 and 28 gauge. The lead distal end or distal portion can have at least one flat face. Electrodes may be disposed on at least one of the flat faces and can have a flat surface in some embodiments of the invention. The electrode metal substrate can be a corrosion resistant, biocompatible and biostable material, such as platinum, platinum alloys, titanium or titanium alloy, gold, etc.

The lead can have 1 or more electrodes (preferably 1-32 and more preferably 4-8 electrodes), with electrical conductors connecting the distal and proximal regions and/or ends, with the proximal region and/or end containing the corresponding number of contacts and configured to be compatible to an implanted pulse generator, or other power source. The electrode dimensions are optimized for battery life by minimizing current loss into undesirable tissue.

The insulation of the lead body, and distal and proximal ends, can be a biocompatible and biostable polymer, such as polyurethane, silicone, polyurethane-silicone hybrid, PEEK™, polyimide, etc.

Figure 1:
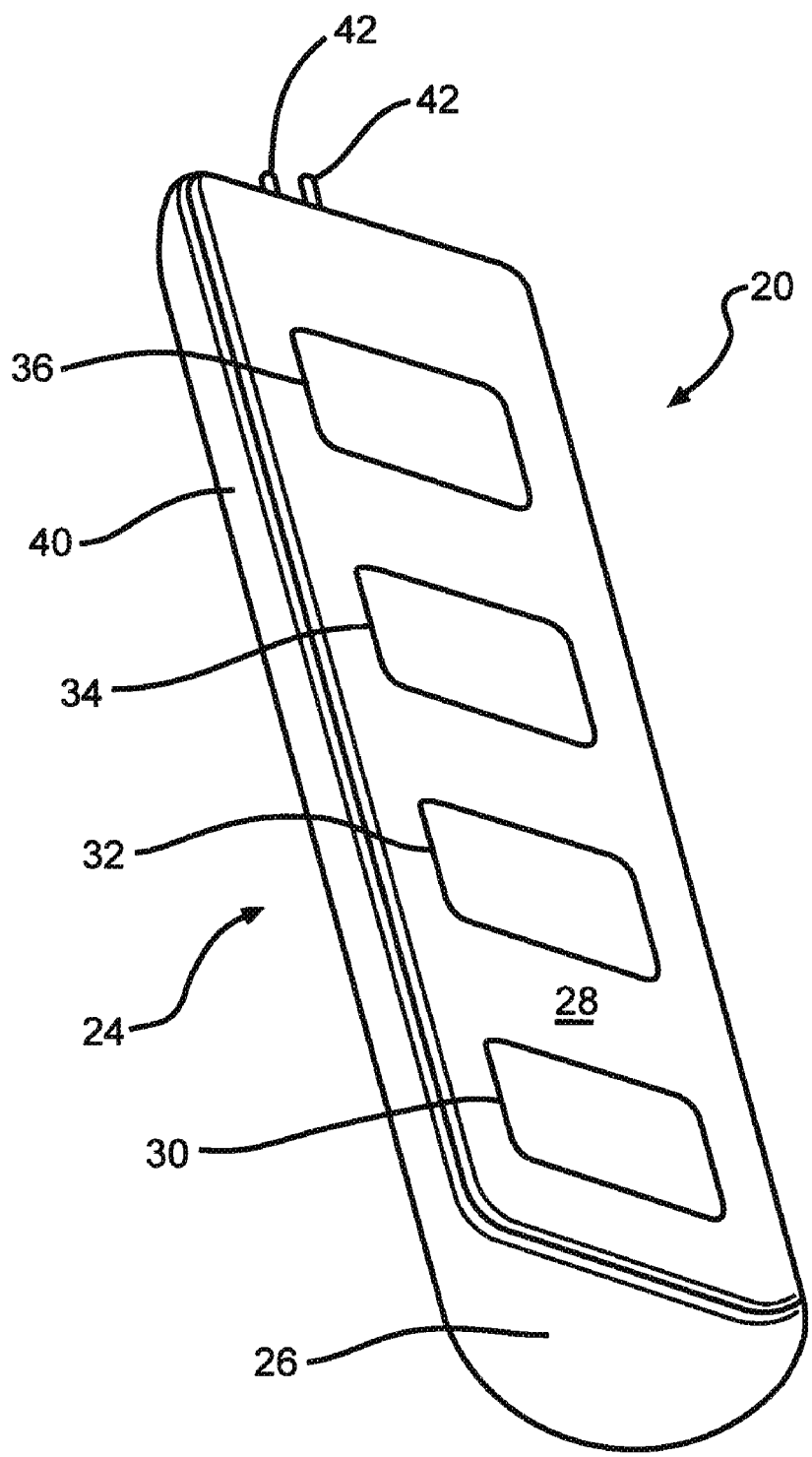
FIG. 1 is a fragmentary, perspective view of a lead distal region in one embodiment, having substantially planar, nominally square shaped electrodes.

FIG. 1 shows one lead 20 according to the present invention, having a polymeric distal region 24 including a housing 40 having four flat surface planar electrodes 30, 32, 34, and 36 disposed within a substantially flat housing region 28. Electrical conductors 42 may be seen in a cutout view extending proximally. Lead 20 terminates in this embodiment in a somewhat rounded distal end 26.

Figure 2:
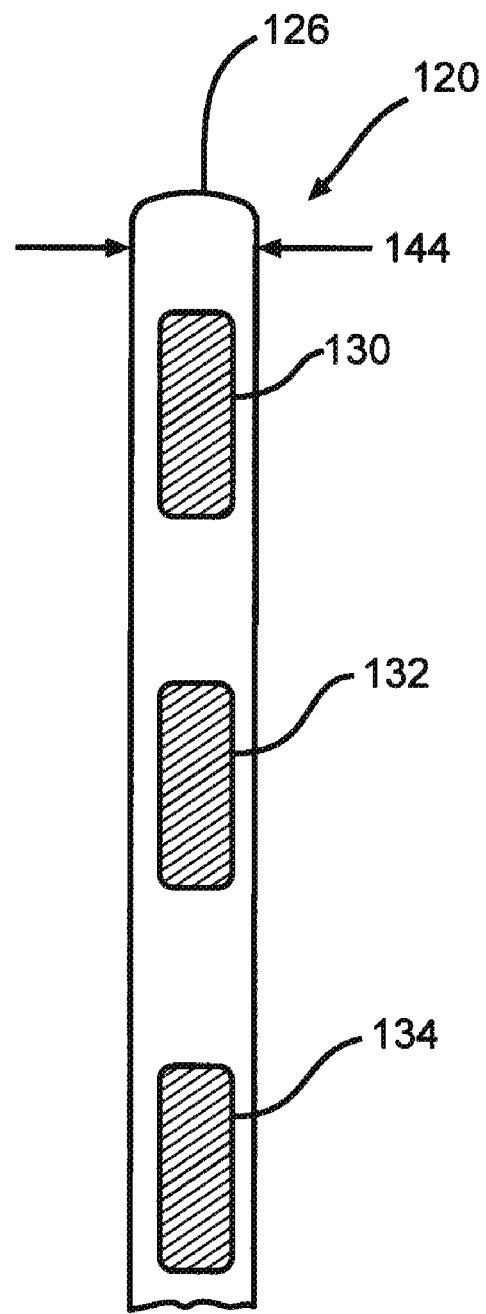
FIG. 2 is a fragmentary, front view of a lead distal region in one embodiment, having substantially planar, nominally rectangular electrodes.

FIG. 2 illustrates another lead embodiment 120 having a width of less than 2 mm, here about 1.3 mm, indicated at 144, and having electrodes 130, 132, and 134 with a surface area of less than about 3 square mm, here about 2 square mm. Lead 120 terminates in a distal tip 126.

Figure 3:
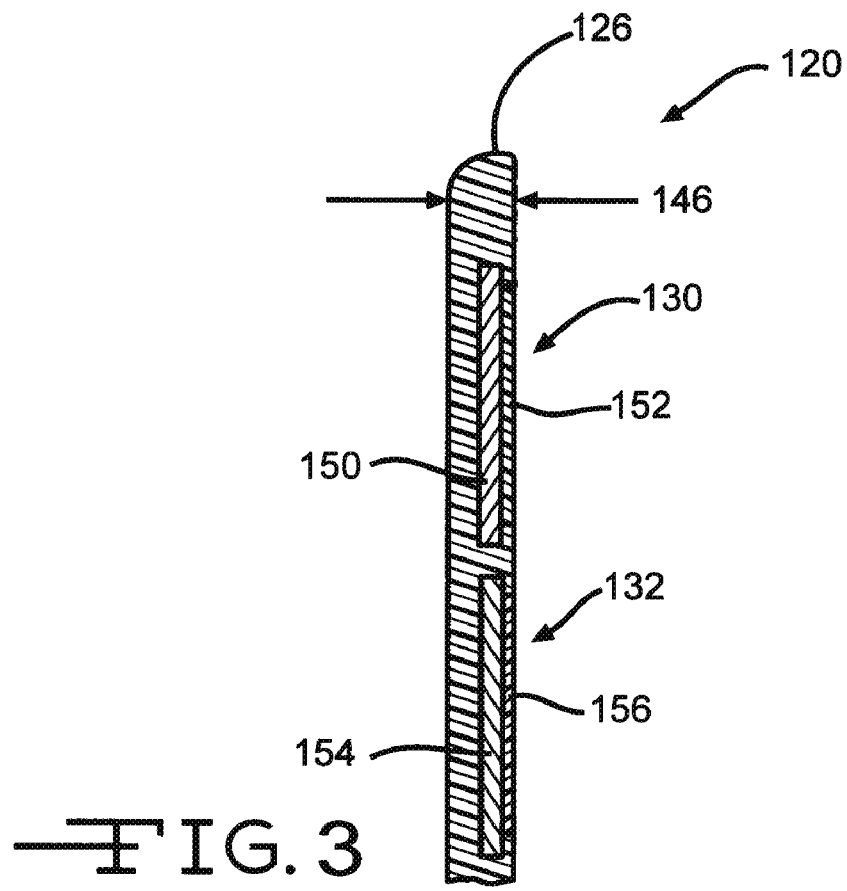
FIG. 3 is a fragmentary, side, cross-sectional view of the lead distal region of FIG. 2, having a polymeric, hydrophilic layer over the electrode metal surface.

FIG. 3 illustrates lead 120 of FIG. 2 in cross section, having a thickness of less than about 1 mm, here about 0.75 mm, indicated at 146. Housing 148 houses a first electrode 130 having a conductor layer and a surface coating or layer 152>which can include a hydrophilic material, steroid, and/or a GABA agonist. A second electrode 132 having a conductor layer 154 with a coating 156 is also shown.

Figure 4:
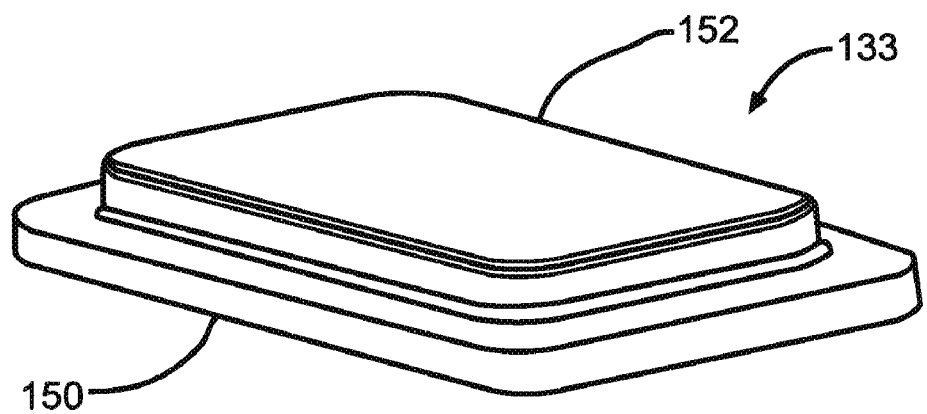
FIG. 4 is a perspective view of one electrode of FIG. 3, having the polymeric hydrophilic layer disposed over the metallic electrode surface.

FIG. 4 illustrates lead electrode 133, having a flat metal substrate 150 coated with a hydrophilic layer 152.

Figure 5:
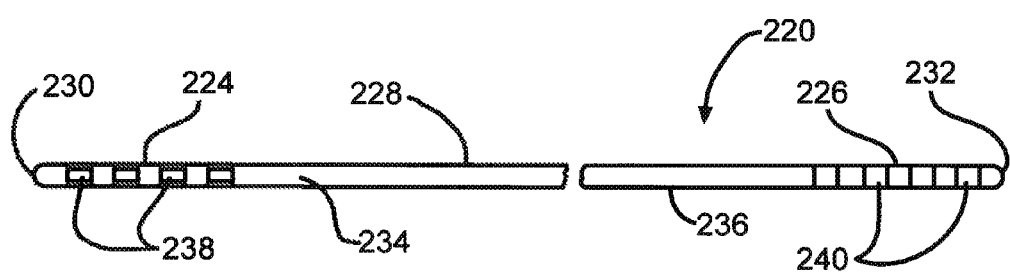
FIG. 5 is a fragmentary, bottom view of a lead according to the present invention having a distal region with four electrodes and a proximal region with four conductor rings.

FIG. 5 illustrates a neurological stimulation lead 220 according to the present invention. Lead 220 can incorporate a multiconductor cable. Lead 220 has a distal region 224 a proximal region 226 and an intermediate region 228 disposed between the distal and proximal regions. In a preferred embodiment, the intermediate region is defined to lie between the innermost distal and proximal electrical contacts described below. Lead 220 can be formed of a body or shaft 234 extending between a distal end 230 and a proximal end 232. Lead body 234 has an exterior surface or side wall 236. In some embodiments, the lead body proximal of the distal region has a substantially round cross section, while in other embodiments the lead regions proximal of the distal region are flat on at least one side, similar to the shape of the distal region bearing the electrodes. Lead body 234 is preferably formed of a polymeric material, for example, polyurethane or silicone.

Lead distal region 224 may include a number of electrodes 238, which may, for example, be cathodes disposed along the bottom of lead body 234 in a spaced-apart configuration. Electrodes 238 may also be described as electrical contacts. Electrodes 238 are normally adapted to be inserted into the human body, are externally exposed, and can be used for neurological stimulation. One exemplary use of electrodes 238 is the stimulation of the nerves within the spinal cord. Proximal region 226 can include a number of connector bands or connector rings 240 disposed in a spaced-apart configuration. Connectors 240 may also be described as electrical contacts or terminals, and are preferably also externally exposed. Connectors may be circumferential or flat, and may be made from platinum, platinum alloys, stainless steel, nickel alloys, etc. Electrodes 238 and connectors 240 may be formed of Platinum and/or Iridium. Connectors 240 can be used for connecting lead 220 to a lead extension to extend the effective length of the lead. In some uses, connectors 240 may also be used to directly couple lead 220 to an implantable pulse generator.

Electrodes 238 and connectors 240 can be coupled to each other in a one-to-one arrangement. In some leads, the distal-most electrode is coupled to the distal-most connector, the second-to-distal-most electrode coupled to the second-to-distal-most connector, and so forth. The electrodes and connectors can be coupled through conductors extending between the two. In some leads, the conductors are embedded within the lead while in other leads, the conductors lie within lumens extending the length of the lead. In some leads, the conductors are disposed within lumens that are later backfilled to substantially fill the lumens with a polymeric material. Some leads have stylet lumens for receiving a stiffening stylet member.

Lead 220 can be varied in outer diameter and length to suit the application for which it is intended. In some embodiments, lead 220 has a total length of between about 5 cm and about 100 cm. In other embodiments, lead 220 has an outer diameter of less than about 1 mm and a total length of between about 10 cm and 150 cm.

Uses for the present invention include, but are not limited to: spinal cord stimulation; brain stimulation; any central nervous system stimulation; any peripheral nerve stimulation; including but not limited to occipital, orbital, cranial, sacral, pudendal, vagus, and/or radial nerves, cardiac pacing and/or defibrillation; smooth muscle stimulation (stomach, liver, etc); and skeletal muscle stimulation.

Leads according to the present invention can be introduced into the epidural space and used to stimulate the spinal cord. In another use, a lead can be introduced into the intrathecal space for spinal cord stimulation. While not wishing to be bound by theory, applicants believe that intrathecal stimulation is not currently used because circumferential electrodes would dump too much current into the highly conductive cerebral spinal fluid. Highly directional electrodes of some embodiments of the present invention, placed in close proximity to the spinal cord, may require much lower current. In some embodiment methods, a GABA agonist coating or layer on the lead distal region: for example, on the electrode, can be placed much closer to the spinal cord when the lead is placed in the intrathecal space. This close proximity to the nerves may increase the effectiveness of the GABA agonist. The GABA agonist coating or coating may also be used in peripheral nerve stimulation. Applicants believe peripheral nerve stimulation may also benefit from the close proximity of the electrode and drug to the nerve.

Various examples and embodiments of the present invention have been presented above, and are intended to illustrate some aspects of the present invention. The scope of the present invention is to be defined by the claims which follow.

What is claimed is:

1. An implantable medical lead comprising:
   a) an elongate lead body having a lead sidewall comprising a non-conducting material extending from a proximal lead portion to a distal lead portion, wherein a cross-section of the distal lead portion perpendicular to a longitudinal axis thereof has a substantially curved section extending to and meeting with a planar surface;
   b) at least one electrical conductor extending between the proximal lead portion and the distal lead portion; wherein the conductor is embedded within the lead body or extends within a lumen within the lead body; and
   c) at least one electrode electrically coupled to the at least one conductor and disposed completely within the planar surface of the lead sidewall in the distal lead portion, the electrode comprising:
      i) an electrode substrate having an upper substrate surface and a lower substrate surface, both extending to a substrate sidewall intermediate the upper and lower substrate surfaces, wherein the substrate sidewall defines a first perimeter;
      ii) a hydrophilic coating supported on the upper substrate surface, the hydrophilic coating having an upper coating surface and a lower coating surface, both extending to a coating sidewall intermediate the upper and lower coating surfaces, wherein the coating sidewall defines a second perimeter; and
      iii) wherein the second perimeter of the hydrophilic coating is spaced inwardly from the first perimeter of the electrode substrate to provide an upper edge of the upper substrate surface that is not contacted by the hydrophilic coating, but is directly contacted by the non-conductive material of the lead body to thereby lock the substrate in place completely within the planar surface of the lead sidewall.

2. The lead of claim 1, wherein the hydrophilic coating has a thickness of at least about 0.0254 mm.

3. The lead of claim 2, further comprising a substance disposed within the hydrophilic coating for diffusion out of the hydrophilic coating, where the substance is a steroid.

4. The lead of claim 3 wherein the steroid is selected from the group consisting of beclamethason, dexamethosone, and their derivatives, and combinations thereof.

5. The lead of claim 2, further comprising a substance disposed within the hydrophilic coating for diffusion out of the hydrophilic coating, where the substance is a GABA agonist.

6. The lead of claim 5, in which the GABA agonist includes baclofen.

7. The lead of claim 2, further comprising a steroid and a GABA agonist disposed within the hydrophilic coating for diffusion out of the hydrophilic coating.

8. The lead of claim 2, in which the hydrophilic coating is swellable in water.

9. The lead of claim 2, in which the coating has a thickness of at least about 0.127 mm.

10. The lead of claim 2, in which the coating has a thickness from about 0.0254 mm to about 0.254 mm.

11. The lead of claim 1 wherein the at least one planar electrode disposed completely within the planar surface of the lead sidewall has a surface area of less than about 3 square mm.

12. The lead of claim 1 wherein the distal lead portion has a width of less than about 2 mm.

13. The lead of claim 1 wherein the distal lead portion has a width of less than about 1.5 mm.

14. The lead of claim 1 wherein the distal lead portion has a thickness less than about 1 mm.

15. The lead of claim 1 wherein the lead is insertable through a needle intended to access a spinal region of a patient.

16. A method for implanting a medical lead, the method comprising:
   a) providing the medical lead comprising:
      i) an elongate lead body having a lead sidewall comprising a non-conducting material extending from a proximal lead portion to a distal lead portion, wherein a cross-section of the distal lead portion perpendicular to a longitudinal axis thereof has a substantially curved section extending to and meeting with a planar surface;
      ii) at least one electrical conductor extending between the proximal lead portion and the distal lead portion; and
      iii) at least one electrode disposed completely within the planar surface of the lead sidewall in the distal lead portion, the at least one electrode being electrically coupled to the at least one conductor, wherein the conductor is embedded within the lead body or extends within a lumen within the lead body; the electrode further comprising an electrode substrate having an upper substrate surface and a lower substrate surface, both extending to a substrate sidewall intermediate the upper and lower substrate surfaces, wherein the substrate sidewall defines a first perimeter, a hydrophilic coating supported on the upper substrate surface, the hydrophilic coating having an upper coating surface and a lower coating surface, both extending to a coating sidewall intermediate the upper and lower coating surfaces, wherein the coating sidewall defines a second perimeter, and wherein the second perimeter of the hydrophilic coating is spaced inwardly from the first perimeter of the electrode substrate to provide an upper edge of the upper substrate surface that is not contacted by the hydrophilic coating, but is directly contacted by the non-conductive material of the lead body to thereby lock the substrate in place completely within the planar surface of the lead sidewall; and
   b) advancing the implantable medical electrical lead to a target site.

17. The method of claim 16 including selecting the target site for peripheral nerve stimulation.

18. The method of claim 17 including selecting the nerve stimulation target from the group consisting of an occipital nerve, a supra orbital nerve, a sub orbital nerve, a pudendal nerve, and combinations thereof.

19. The method of claim 16 including eluting a steroid from the hydrophilic coating disposed over the lead conductor.

20. The method of claim 16 including eluting a GABA agonist from the hydrophilic coating disposed over the lead conductor.

21. The method of claim 20 wherein eluting the GABA agonist includes eluting baclofen.

22. The method of claim 16 including advancing the lead to the target site being the epidural space.

23. The method of claim 16 including advancing the lead to the target site being the intrathecal space.

24. The method of claim 16 further including eluting a GABA agonist within the intrathecal space from the hydrophilic coating.

25. The method of claim 16 including advancing the implantable electrical medical lead through a needle to the target site.

26. The needle of claim 25 wherein the needle being of a size less than 12 gauge.

27. The method of claim 16 including connecting the proximal lead portion to a pulse generator implanted in body tissue.

28. The method of claim 16 including stimulating a body tissue at the target site with electrical current delivered from a pulse generator, through the at least one electrical conductor of the lead and out the at least one electrode.

29. The method of claim 16 including providing, the hydrophilic coating having a thickness of at least about 0.0254 mm.

30. An implantable medical electrical lead, comprising;
   a) an elongate lead body having a lead sidewall comprising a non-conducting material extending from a proximal lead portion to a distal lead portion, wherein a cross-section of the distal lead portion perpendicular to a longitudinal axis thereof has a substantially curved section extending to and meeting with a planar surface;
   b) at least four electrical conductors extending between the proximal lead portion and the distal lead portion; wherein the conductor is embedded within the lead body or extends within a lumen within the lead body;
   c) at least four electrodes disposed completely within the planar surface of the lead sidewall in the distal lead portion, the at least four electrodes each being electrically coupled to at least one of the at least four conductors, wherein each electrode comprises:
      i) an electrode substrate having an upper substrate surface and a lower substrate surface, both extending to a substrate sidewall intermediate the upper and lower substrate surfaces, wherein the substrate sidewall defines a first perimeter;
      ii) a hydrophilic coating supported on the upper substrate surface, the hydrophilic coating having an upper coating surface and a lower coating surface, both extending to a coating sidewall intermediate the upper and lower coating surfaces, wherein the coating sidewall defines a second perimeter; and
      iii) wherein the second perimeter of the hydrophilic coating is spaced inwardly from the first perimeter of the electrode substrate to provide an upper edge of the upper substrate surface that is not contacted by the hydrophilic coating, but is directly contacted by the non-conductive material of the lead body to thereby lock the substrate in place completely within the planar surface of the lead sidewall.

31. The implantable lead of claim 30 wherein a steroid is disposed within the hydrophilic coating for diffusion therefrom and wherein the steroid is selected from the group consisting of beclamethason, dexamethosone, their derivatives, and combinations thereof.

32. The implantable lead of claim 30 wherein a GABA agonist is disposed within the hydrophilic coating for diffusion therefrom.

33. The lead of claim 30 wherein the lead is insertable through a needle intended to access a spinal region of a patient.

34. The lead of claim 30 further comprising a space between each electrode.

* * * * *